United States Patent [19]

Brady

[11] Patent Number: 4,663,435

[45] Date of Patent: May 5, 1987

[54] BRIDGED CYCLIC HEXAPEPTIDE SOMATOSTATIN ANALOGS

[75] Inventor: Stephen F. Brady, Philadelphia, Pa.

[73] Assignee: Merck & Co., Inc., Rahway, N.J.

[21] Appl. No.: 748,069

[22] Filed: Jun. 24, 1985

Related U.S. Application Data

[63] Continuation of Ser. No. 446,938, Dec. 6, 1982, abandoned.

[51] Int. Cl.$^4$ .......................... C07K 7/26; C07K 5/12; A61K 37/24
[52] U.S. Cl. .................................. 530/311; 530/317; 514/806; 540/482
[58] Field of Search ................. 260/112.5 R; 530/311, 530/317; 514/10, 806; 540/482

[56] References Cited

U.S. PATENT DOCUMENTS

| | | | |
|---|---|---|---|
| 3,842,067 | 10/1974 | Sarantakio | 260/112.55 |
| 3,972,859 | 8/1976 | Fujino et al. | 260/112.52 H |
| 4,139,526 | 2/1979 | Veber | 260/112.55 |
| 4,235,886 | 11/1980 | Freidinger et al. | 260/112.55 |
| 4,310,518 | 1/1982 | Freidinger et al. | 260/112.53 |

FOREIGN PATENT DOCUMENTS

0029579  3/1981  European Pat. Off. ......... 260/112.5

OTHER PUBLICATIONS

Brady, et al., Med. Chem. Symposium (Presentation). Life Sciences 34, 1371-1378 (1984).

*Primary Examiner*—Delbert R. Phillips
*Attorney, Agent, or Firm*—David L. Rose

[57] ABSTRACT

Somatostatin analogs are prepared wherein a cyclic hexapeptide contains a bridged grouping which replaces eight of the ring amino acids of somatostatin. The bridged cyclic hexapeptides are easier to synthesize, have a longer duration of activity, and many have a greater level of activity than somatostatin. The compounds have the properties of selectively inhibiting the release of glucagon, growth hormone and insulin. Certain of the compounds also are capable of inhibiting the release of gastric acid secretions. The compounds are particularly useful in the treatment of acromegaly, diabetes, diabetic retinopathy and peptic ulcers. These bridged cyclic hexapeptides are prepared by the solid phase method.

13 Claims, No Drawings

BRIDGED CYCLIC HEXAPEPTIDE SOMATOSTATIN ANALOGS

This is a continuation of application Ser. No. 446,938, filed Dec. 6, 1982, now abandoned.

BACKGROUND OF THE INVENTION

Somatostatin is a tetradecapeptide incorporating a cyclic dodecapeptide, having the structure:

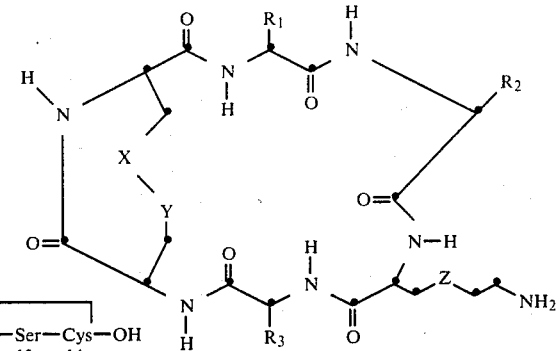

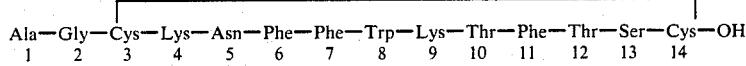

and has the properties of inhibiting the release of growth hormone, inhibiting the release of insulin and glucagon and reducing gastric secretions. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself.

SUMMARY OF THE INVENTION

The present invention provides for bridged, preferably disulfide bridged cyclic hexapeptides which are derivatives of somatostatin in which, inter alia, eight of the ring amino acids are replaced by Cys-Cys or cystathionyl groupings and both of the exocyclic amino acids are removed. Further substitution and reaction of the remaining amino acids is also described. The bicyclic hexapeptides inhibit the release of glucagon, growth hormone and insulin, and inhibit the release of gastric acid secretions. Specifically the compounds may preferentially inhibit the release of growth hormone without affecting the level of gastric secretions alone or without affecting the level of gastric secretions, insulin and glucagon; or the compounds may inhibit the release of gastric acid secretions. Thus, the compounds have a more selective biological activity than somatostatin. The bridged cyclic hexapeptide compounds of the instant invention also have a longer duration of activity than somatostatin. As such the instant cyclic hexapeptides are useful for the treatment of acromegaly, diabetes, diabetic retinopathy and peptic ulcers.

Thus, it is an object of the present invention to describe the bridged cyclic hexapeptide somatostatin analogs, particularly the disulfide bridged compounds. A further object is to describe procedures for the preparation of such bridged cyclic hexapeptides. A still further object is to describe the use of such compounds in the treatment of acromegaly, diabetic retinopathy and peptic ulcers. Further objects will become apparent from reading the following description.

DESCRIPTION OF THE INVENTION

The compounds of the instant invention are best realized in the following structural formulae:

wherein
X and Y are S or $CH_2$ provided at least one of X and Y is S;
Z is $(CH_2)_m$ wherein m is 0, 1 or 2 or sulfur such that the sulfur may be in any position along the chain;
$R_1$ is loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;
$R_2$ is 3-indolylmethyl or substituted 3-indolylmethyl wherein the substituent may be loweralkyl, loweralkoxy, or halogen;
$R_3$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro.

The term "loweralkyl" when used in the instant application is intended to represent those alkyl groups either straight or branched chain, which have from 1–5 carbon atoms. Examples of such alkyl groups are methyl, ethyl, propyl, iso-propyl, butyl, sec-butyl, pentyl and the like.

The term "loweralkoxy" is intended to include those alkoxy groups of from 1–5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" is intended to include fluorine, chlorine, bromine and iodine.

The term "5- or 6-membered heterocyclic ring" is intended to include those 5- and 6-membered heterocycles with 1- or 2-heteroatoms selected from oxygen, nitrogen and sulfur. Exemplary of such heterocycles is imidazole, furan, thiazole, pyrazole, pyridine and the like.

In the instant compounds there are several asymmetric centers which will lead to the existence of optical isomers for such compounds. In the instant invention, for each of the asymmetric centers of the various amino acids which make up the instant cyclic hexapeptides, both the D and L configurations are intended to be encompassed.

It will be appreciated by those skilled in the art that when $R_1$ is benzyl, $R_2$ is indolylmethyl, Z is methylene, and $R_3$ is 1-hydroxyethyl, the 7, 8, 9 and 10 amino acids of somatostatin (-Phe-Trp-Lys-Thr) are represented, and the Cys-Cys grouping with its bridges linkage has taken the place of the remainder of the somatostatin amino acids. Thus, using the above difinitions of the substituent groups, the following representative cyclic hexapeptide analog of somatostatin is formed in structure I;

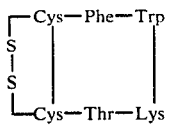

The preferred embodiments of the cyclic hexapeptides of this invention are realized in the foregoing structural formula I wherein X and Y are sulfur and Z is $(CH_2)_m$ and m is 1;

$R_1$ is as defined above;

$R_2$ is 3-indolylmethyl or substituted indolylmethyl wherein the substituent is methoxy or fluoro; and $R_3$ is methyl, ethyl, hydroxy methyl or hydroxy ethyl.

Further preferred embodiments are realized when Z is methylene;

$R_1$ is as defined above;

$R_2$ is 3-indolylmethyl; and $R_3$ is hydroxy ethyl.

The preferred $R_1$ groups are loweralkyl, benzyl or substituted benzyl where the substituent is loweralkyl, halogen, hydroxy, amino, nitro or alkoxy.

Included within these preferred disulfide bridged compounds are:

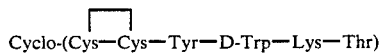

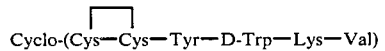

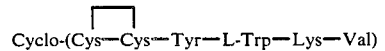

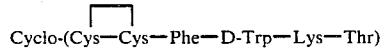

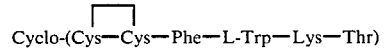

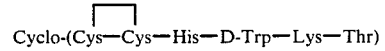

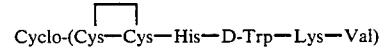

In the instant application several abbreviated designations are used for the amino acid components, certain preferred protecting groups, reagents and solvents. The meanings of such abbreviated designations are given in Table I.

TABLE I

| Abbreviated Designation | |
|---|---|
| | Amino Acid |
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| Val | L-valine |
| Abu | L-α-aminobutyric acid |
| Ser | L-serine |
| Asn | L-asparagine |
| Pro | L-proline |
| Asu | D- or L-aminosuberic acid |
| Cys | L-cysteine |
| | Protecting Groups |
| INOC | isonicotinyloxycarbonyl |
| BOC | tert-butyloxycarbonyl |
| OMe | methyl ester |
| Bu | tert-butyl |
| CBZ | benzyloxycarbonyl |
| Bzl | benzyl |
| 2-Cl—CBZ | 2-chlorobenzyloxycarbonyl |
| Acm | acetamidomethyl |
| Me | methyl |
| | Activating Groups |
| ONp | p-nitrophenyl ester |
| HSE | N—hydroxysuccinimide ester |
| HBT | 1-hydroxybenzotriazole |
| | Condensing Agents |
| DCCI | dicyclohexylcarbodiimide |
| | Reagents |
| TFA | trifluoroacetic acid |
| TEA | triethylamine |
| DIPEA | diisopropylethylamine |
| | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel disulfide bridged cyclic hexapeptide somatostatin analogs are prepared by cyclizing corresponding linear peptides. The linear peptides are prepared by using the solid phase sequential synthesis technique. Accordingly, the process for preparing the disulfide bridged cyclic hexapeptide somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic hexapeptide through the formation of an amide bond; (e) removing any side chain blocking groups, and (f) treating the cyclic peptide with a reagent to remove the cysteine sulfur-protection and allow closure to give the bicyclic final product.

When the linear peptide is prepared on the resin, it is generally not critical which amino acid is selected to be at the C-terminal position provided only that the sequence of amino acids in the linear peptide corresponds to that in the desired somatostatin analog. Once a linear peptide has been cyclized one can on longer determine which amino acid was at the C-terminus of the linear peptide.

While generally the selection of the first amino acid to start the chain is not critical, since the linear peptide will be cyclized, there may be other factors which may cause one to prefer one starting amino acid over another. For example D-Trp can react with t-butyl carbonium ions which are formed with BOC groups are removed. Thus, selection of a reaction sequence which places D-Trp at the N-terminal end of the linear peptide will cause D-Trp to be added last, and thus it will have the least exposure to t-butyl carbonium ions. This type of selection may not always be possible, such as where there are two indole containing moieties in the peptide. However, such reaction sensitivities should be considered when planning a peptide reaction sequence.

The synthesis of the linear peptides by the solid phase technique is conducted in a stepwise manner on chloromethylated resin. The resin is composed of fine beads (20-70 microns in diameter) of a synthetic resin prepared by copolymerization of styrene with 1-2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoro acetic acid, or hydrogen chloride in ethyl acetate).

The sulfur of cysteine can be protected with the acetamidomethyl (Acm). A particular advantage of the Acm group is that it is not removed by treatment with HF and remains intact, to allow the isolation of the bridged cyclic hexapeptide in a sulfur-protected form at the penultimate stage. The Acm group is removed as part of the procedure leading to the disulfide bridged bicyclic final product. The second cyclization which prepares the bridging structure is accomplished with iodine in N,N-dimethylformamide or alternatively, by mercuric ion followed by air oxidation.

The OH group of Thr and Ser can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide ahs been cyclized. The INOC group is not removed by HF and requires an additional treatment with Zn. Neither group is affected by TFA, used for removing BOC protecting groups. After the linear peptide is cyclized, the protective groups, such as 2-Cl-CBZ and Bzl, are removed by treatment with HF.

After the linear peptide has been formed on the solid phase resin, it may be removed from the resin by a variety of methods which are well known in the art. For example, the peptide may be cleaved from the resin with hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about $-40°$ C. and $+20°$ C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired cyclic peptide. The preferred method for cleaving the peptide from the resin in the present invention is the use of hydrazine.

In those compounds wherein one of X or Y is methylene, the final products containing the —S—CH$_2$— or —CH$_2$—S— bridging group are prepared by using one of the following cyclic dipeptides as one of the amino acids in the solid phase synthesis:

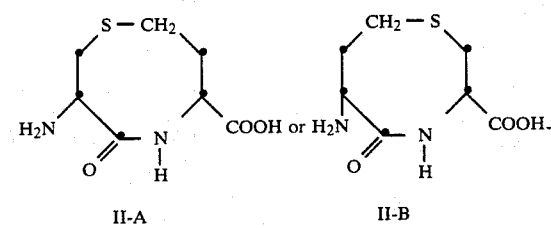

II-A                II-B

In this manner the normally linear peptide which is prepared by the solid phase technique is made as a cyclic compound with the bridging group already in place. From the solid phase series of reactions the above cyclic dipeptides will have the other four amino acids substituted on the amino or carboxyl acid group or both. The distribution can be in any pattern with all of the other four amino acids on the amino, all on the carboxylic acid or distributed on both. When the monocyclic hexapeptide is cyclized the original order of the amino acids will be observed, as discussed above. In addition, since the bridging group is already in place, the final cyclization, used for the disulfide bridging group, is not necessary, and the bicyclic hexapeptide is formed directly.

Both bicyclic dipeptides II-A and II-B may be obtained from the same precursor, L-cystathionine, by direct cyclization using methods known in the art. The two possible dipeptide components are separated from any polymeric by-products using standard techniques, preferably, however, with gel filtration. They may be separated from one another by any of a variety of techniques known in the art, preferably silica gel chromatography.

The thus produced amino acid is protected at the amino group, preferably, by t-BOC, for incorporation into the linear hexapeptide sequence, in place of -Cys-(Acm)-Cys(Acm)- using the solid phase technique. Removal from the solid support by hydrazinolysis, cyclization and blocking group removal affords the desired bicyclic product directly.

As reference Table II will show, one preferred overall procedure for preparing the desired disulfide bridged cyclic hexapeptides of the present invention involves the stepwise synthesis of the linear peptide on a solid phase resin. More specifically, in the process for preparing compound III:

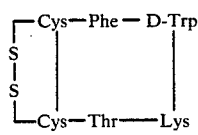 III the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in CH₂Cl₂. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence:

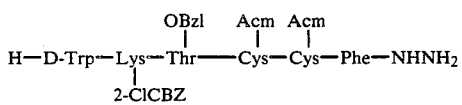

is treated with isoamyl nitrite in acid pH to form the corresponding azide. The azide solution is diluted with solvent and neutralized with an organic base. The linear peptide cyclizes to form:

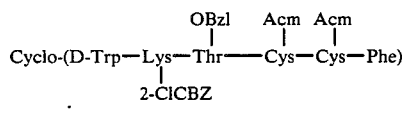

During the cyclization the pH is checked and maintained at neutral by the addition of organic base. The pH in organic solvent is determined by the application of an aliquot of the solution to moistened narrow range pH paper.

After the linear peptide is cyclized, the protective groups, 2-Cl-CBZ and OBzl, are removed by treatment with HF in the presence of anisole, and the Acm groups are removed and the disulfide bridge is simultaneously created by reacting the Acm-protected cyclic hexapeptide with iodine in N,N-dimethylformamide. The crude disulfide bridged cyclic peptide obtained is purified chromatographically, preferably by gel filtration. One example of such gel filtration is passing a solution to be purified through a column of Sephadex (a cross-linked dextran gel) and eluting with 50% acetic acid or with 2N-acetic acid. The elution of the desired product is determined by analyzing aliquots of the material using thin layer chromatography.

TABLE II

The reaction scheme for the preparation of one of the disulfide bridged cyclic hexapeptides of this invention is outlined in the following series of reactions:

Reaction scheme for preparing:

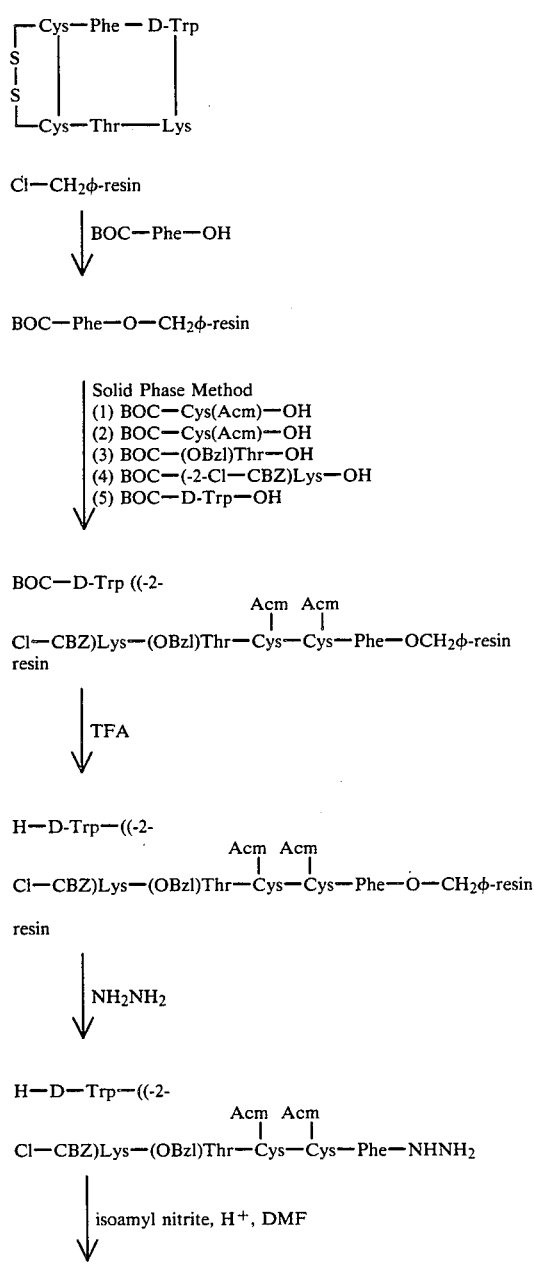

TABLE II-continued

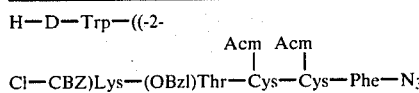

H—D—Trp—((-2-Cl—CBZ)Lys—(OBzl)Thr—Cys(Acm)—Cys(Acm)—Phe—N₃

↓ DMF/triethylamine

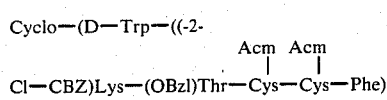

Cyclo—(D—Trp—((-2-Cl—CBZ)Lys—(OBzl)Thr—Cys(Acm)—Cys(Acm)—Phe)

↓ HF/Anisole

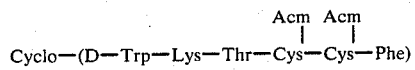

Cyclo—(D—Trp—Lys—Thr—Cys(Acm)—Cys(Acm)—Phe)

↓ I₂/DMF

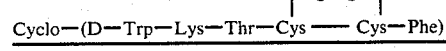

Cyclo—(D—Trp—Lys—Thr—Cys—S—S—Cys—Phe)

The following examples are given to illustrate the methods used to carry out the present invention. It is to be understood that these examples are given for purposes of illustration and not limitation.

EXAMPLE 1

Preparation of
H-D-Trp-(ε-2-Cl-CBZ)Lys-(OBzl)Thr-Cys(Acm)-Cys-(Acm)-Phe-OCH₂φ-resin Chloromethyl resin (2% cross-linked Merrifield resin), 862.0 g (2.37 moles), having 2.75 meq. chlorine/g, and 607.0 g (2.37 moles, 1 equivalent of BOC-Phe-OH were added to 4320 ml of peroxide-free tetrahydrofuran. The mixture was stirred in an oil bath at 80° C. bath temperature for 45 minutes. Triethylamine, 310.0 ml, was added and the reaction mixture stirred at 80° C. bath temperature for 70 hours, cooled to 25° C. and transferred to a stirred solid phase reaction column with 2000 ml of tetrahydrofuran. After removal of the solvent, the resin was washed using the stirred column with:

3×2000 ml of tetrahydrofuran
4×5170 ml of ethanol
1×5170 ml of acetic acid
3×5170 ml of water
3×5170 ml of methanol
3×5170 ml of chloroform The BOC-Phe-O-CH₂φ-resin was dried in vacuo at 25° C. for 16 hours, giving 1203 g of BOC-Phe-O-CH₂O-resin containing 1.2 mmole of phenylalanine/g of resin.

BOC-Phe-O-CH₂φ-resin (1.65 g; 2.0 mmole) was carried through the procedures in Tables III and IV using 2 deblockings (2 minutes and 25 minutes) with 25% TFA in methylene chloride and 2.5 equivalents of BOC-amino acid in the required sequence until the desired BOC-hexapeptide-O-CH₂φ-resin was obtained.

DCCI was used as the sole coupling agent in every step.

The coupling of each amino acid proceeded smoothly. Best yields were obtained when the coupling was repeated in each step. When the coupling was repeated, the initial two chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl and the ε-amino group of Lys with 2-Cl-CBZ.

When the desired BOC-hexapeptide-O-CH₂φ-resin was obtained, the N-terminal BOC group was removed by the terminal deblocking procedure set forth in Table V.

TABLE III

| Solvent or reagent (number of treatments or washes) | CHCl₃ (2) | 25% TFA in CH₂Cl₂ (2) | CHCl₃ (3) | NEt₃—CH₂Cl₂ (1:9) (2) | CHCL₃ (3) CH₂Cl₂ (3) | BOC AA in CH₂Cl₂ DMF or a mixture of both | 0.5 M DCCI in CH₂Cl₂ | DMF (1) MeOH (1) DMF (1) MeOH (1) CHCl₃ (2) |
|---|---|---|---|---|---|---|---|---|
| Vol. in ml | 40 | 20 | 40 | 40 | 40 | 25 | 10 | 40 |
| Time in min. | 5 | 2 and 25 | 2 | 5 and 5 | 2 | 5 | 5 coupling 30 | 2 |

TABLE IV

| Protected Amino Acid | Solvent Ml |
|---|---|
| BOC—Cys(Acm) Recouple | 20 ml CH₂Cl₂ |
| BOC—Cys(Acm) Recouple | 20 ml CH₂Cl₂ |
| BOC (OBzl)Thr (1.55 g) Recouple | 20 ml CH₂Cl₂ |
| BOC—(ε2-Cl—CBZ)Lys (2.24 g) Recouple | 20 ml CH₂Cl₂ |
| BOC—D-Trp (1.52 g) Recouple | 15 ml CH₂Cl₂, 5 ml DMF |

TABLE V

TERMINAL DEBLOCKING PROGRAM

| Solvent or reagent (number of treatments or washes) | CHCl₃ (1) | 25% TFA in CH₂Cl₂ + 1% Ethanedithiol (2) | CHCl₃ (3) | MeOH (2) CH₂Cl₂ (1) MeOH (2) CH₂Cl₂ (2) |
|---|---|---|---|---|
| Vol. in ml. | 40 | 40 | 40 | 40 |
| Time in minutes | 5 | 2 and 25 | 2 | 2 |

After the procedures of Tables III, IV and V were completed, the blocked hexapeptide-OCH₂-φ-resin is dried overnight and weighs 4.00 g.

EXAMPLE 2

Preparation of D-Trp-(ε-2-Cl-CBZ)Lys-(OBzl)Thr-Cys(Acm)-Cys-(Acm)-Phe-NHNH₂

The resin from Example 1 was combined with 36 ml of a 9:1 mixture of N,N-dimethylformamide and hydrazine and stirred at room temperature for 1 hour. The insoluble resin was removed by filtration and the solution was evaporated to remove the N,N-dimethylformamide. The addition of 50 ml of water followed by trituration gave a solid. The solid was isolated by filtration, and washed thoroughly with water. The solid was dried in vacuo and weighed 2.46 g.

EXAMPLE 3

Preparation of H-D-Trp-(ε-2-Cl-CBZ)Lys-(OBzl)Thr-Cys(Acm)-Cys-(Acm)-Phe-N₃

2/41 G of the product from Example 2 was combined with 40 ml of degassed N,N-dimethylformamide under a blanket of nitrogen, cooled to −10° C., and 5 equivalents of 5.9M hydrogen chloride in 2.0 ml of tetrahydrofuran was added. The solution was cooled to −25° C. and 0.31 ml of a isoamyl nitrite was added in portions until a positive starch/KI test was obtained. The completion of the reaction was determined by thin layer chromatography and the disappearance of the hydrazide starting material.

EXAMPLE 4

Preparation of Cyclo(D-Trp-(ε-2-Cl-CBZ)Lys-(O-Bzl)Thr-Cys(Acm)-Cys(Acm)-Phe)

The solution of the azide compound of Example 3 was added to 1.2 l of degassed dimethylformamide, precooled to −25° C., the pH adjusted to 8, with diisopropylethylamine, and the reaction mixture placed in the freezer (−25° C.) overnight. The pH was readjusted to 8 if necessary after about 14 hours and the mixture stored for 16 hours at −20° C. and 16 hours at 5° C. Thin layer chromatography indicated that the reaction was complete. The mixture was concentrated to dryness, and the residue was triturated with 50 ml of water to give a white solid. The solid was isolated by filtration, washed with water and dried in vacuo. The product weighed 2.30 g.

EXAMPLE 5

Preparation of Cyclo(D-Trp-Lys-Thr-Cys(Acm)-Cys(Acm)-Phe)

2.03 G (1.7 mmoles) of the protected cyclic hexapeptide of Example 4 was combined in a teflon lined chamber with 2 ml of anisole. The chamber was then evacuated and filled with 20 ml of liquid hydrogen fluoride at the temperature of the dry ice/acetone bath. The temperature was raised to 0° C. and stirred for 1 hour. The hydrogen fluoride was allowed to evaporate and the residue placed in vacuo until a slurry was formed. The slurry was treated with 50 ml of ethyl acetate and filtered affording 1.87 g of a fine powder. The crude product was dissolved in 50% acetic acid, placed on a column of Sephadex G-25 gel (superfine) and eluted with the same solvent. The presence of the product in the eluent was determined by thin layer chromatographic analysis. The residue after evaporation of the pooled fractions and freeze drying, afforded 1.17 g of product.

EXAMPLE 6

Preparation of

Cyclo-(D-Trp—Lys—Thr—Cys⎯S—S⎯Cys—Phe)

254 Mg of iodine (1.0 mmole) was dissolved in 90 ml of freshly degassed DMF and added to a solution of 182 mg (0.2 mmole) of the product of Example 5 dissolved in 90 ml of freshly degassed DMF. The mixture was stirred for 3½ minutes and 600 mg of zinc dust and 40 ml of 50% aqueous acetic acid at 0° C. was added with stirring. The temperature spontaneously rose to 30° C. The reaction was decolorized with carbon, filtered and the filtrate washed twice with DMF. The solution was evaporated to dryness, dissolved in 50% aqueous acetic acid and placed on a column of Sephadex G-25 gel (superfine) eluted with the same solvent affording 66.9 mg of product.

The sample thus isolated was found to be unstable with respect to polymerization in certain solvents or on extended storage. In order to stabilize the compound toward such decomposition it was treated in aqueous solution with 10–40 mole % of N-ethylmaleimide, a reagent which will react with free sulfhydryl groups that could catalyze disulfide interchange. The excess N-ethyl maleimide was separated by passage through a column of Sephadex G-25 gel (superfine) eluted with 50% acetic acid. The peptide was reisolated by freeze-drying of the pooled column fractions after evaporation and shown to be completely stable.

Following the above procedure, either Examples 1–6 or 1–5 and 7 and by modifying only the selection and order of amino acids in the process of Example 1, there are prepared other cyclic hexapeptides of this invention.

The instant cyclic hexapeptide analogs of somatostatin are tested and compared with the effects of somatostatin in an in vitro test for the inhibition of growth hormone. The test is described as follows:

"Rat pituitaries were isolated according to the procedures of Vale and Grant 'In Vitro Pituitary Hormone Secretion Assay for Hypophysiotropic Substances' in Methods in Enzymology. Vol. XXXVII, eds. O'Malley, B. W. and Hardman, J. G. (Academic Press, Inc., New York) pp. 5–93 (1975).

After 4 days in culture, the cells were washed and incubated for 4 hours in Dulbecco-modified Eagle's medium in the presence or absence of graded doses of each analog or somatostatin. The medium was then collected for subsequent growth hormone determination by a double antibody radioimmunoassay for rat growth hormone."

EXAMPLE 7

Preparation of

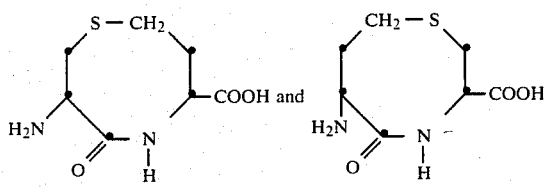

A solution of 222 mg of L-cystathionine in 500 ml of DMF at 0° is treated with TEA to give a pH of 7.5 (as determined by moistened narrow-range pH paper), followed by 0.24 ml of diphenylphosphoryl azide (DPPA). Stirring is maintained and TEA is added periodically to maintain pH 7.5. Completion of the reaction is determined by thin layer chromatography and the disappearance of the starting material. The solvent is removed by evaporation, and the residue is dissolved in 50% acetic acid and placed onto a column of Sephadex G-25 gel. Elution is accomplished with the same solvent to afford a mixture of the two desired monocyclic monomeric products. These components are separated by silica gel or ion exchange chromatography, and isolated independently by freeze-drying.

The compounds thus isolated may be suitably protected and employed as one of the amino acids reacted with the resin-bound peptide in Example 1 and carried through to Example 5. The cyclization process of Example 6 is not employed since the thiomethylene bridge analog to the disulfide bridge is prepared above in an early step in the synthesis and not reserved for the end of the synthesis as is the formation of the disulfide bridge.

Analogs of somatostatin were compared to somatostatin in their ability to decrease the levels of portal vein glucagon and insulin in anesthetized rats. Male Sprague-Dawley rats (Charles River CD) weighing 160–200 g were anesthetized with urethane (150 mg/100 g of body weight; Aldrich). Saline or peptides were adminstered via the external jugular vein. After 5 minutes, the portal vein was exposed, and blood was collected via syringe containing 3 mg of EDTA and placed in chilled tubes containing 100 μl of Trasylol (FBA Pharmaceuticals) for subsequent hormone analysis. Plasma levels of glucagon were determined by the method of Faloona and Unger, *Methods of Hormone Radioimmunoassay*, Jaffe and Behrman (Eds), Academic Press, New York, Vol. II, pp. 257–527 (1976), utilizing glucagon antisera 30K obtained from R. Unger (Dallas, TX). Plasma levels of insulin were determined by a modification of the procedure of Herbert et al., *J. Clin. Endocrinol. Metab.*, 25, 1375–1384 (1965).

The test results for some of the compounds of this invention are recorded below with the results for somatostatin listed first and given the arbitrary value of 1. The results for the instant compounds are given as multiples or fractions of the effect of somatostatin. The numbers in parentheses are the fiducial limits for the number preceding. The first of the instant compounds listed is the compound prepared in Examples 1-5. The compound is written slightly different, however, to conform to the order of the amino acids found in somatostatin.

| Activity of Cyclichexapeptide Analogs of Somatostatin | | | |
|---|---|---|---|
| Compound | Growth Hormone Release Inhibition | Insulin Inhibition | Glucagon Inhibition |
| Somatostatin | 1 | 1 | 1 |
| Cyclo(Cys—Cys—Phe—D—Trp—Lys—Thr) | 2.47(1.66-3.81) | 10.6(5.5-19.9) | Active |

What is claimed is:

1. A compound having the formula:

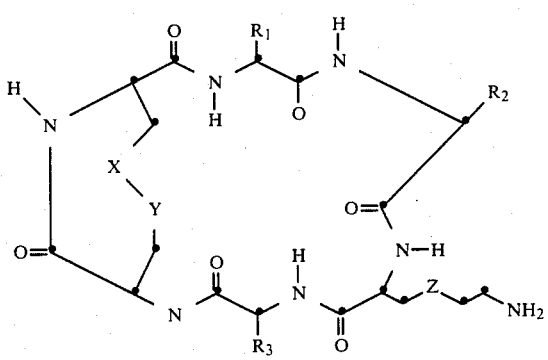

wherein

X and Y are S or $CH_2$ provided at least one of X and Y is S;

Z is $(CH_2)_m$ wherein m is 0, 1 or 2 or sulfur such that the sulfur may be in any position along the chain;

$R_1$ is lower alkyl, benzyl, substituted benzyl wherein the substituent may be one or two of loweralkyl, halogen, hydroxy, amino, nitro or loweralkoxy; and loweralkyl substituted with a 5- or 6-membered heterocyclic ring;

$R_2$ is 3-indolylmethyl or substituted 3-indolylmethyl wherein the substituent may be loweralkyl, loweralkoxy or halogen;

$R_3$ is loweralkyl, hydroxyloweralkyl, benzyl, carboxyloweralkyl, aminoloweralkyl or substituted hydroxy benzyl wherein the substituent may be loweralkyl, loweralkoxy, hydroxy, halogen, amino or nitro.

2. A compound of claim 1 wherein Z is $(CH_2)_n$ and n is 1;

$R_1$ is as defined in claim 1;

$R_2$ is 3-indolylmethyl or substituted indolylmethyl wherein the substituent is methoxy or fluoro; and $R_3$ is methyl, ethyl, hydroxymethyl or hydroxyethyl.

3. A compound of claim 1 wherein:

Z is methylene;

$R_1$ is as defined in claim 1;

$R_2$ is 3-indolylmethyl; and $R_3$ is hydroxyethyl.

4. The compound of claim 2 which is cyclo

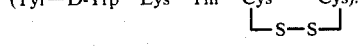

5. The compound of claim 2 which is cyclo (Phe—D-Trp—Lys—Thr—Cys———Cys).
         └─S—S─┘

6. The compound of claim 2 which is cyclo (Phe—L-Trp—Lys—Thr—Cys———Cys).
         └─S—S─┘

7. The compound of claim 2 which is cyclo (Tyr—D-Trp—Lys—Val—Cys———Cys).
         └─S—S─┘

8. The compound of claim 2 which is cyclo (Tyr—L-Trp—Lys—Val—Cys———Cys).
         └─S—S─┘

9. The compound of claim 2 which is cyclo (His—D-Trp—Lys—Thr—Cys———Cys).
         └─S—S─┘

10. The compound of claim 2 which is cyclo (His—D-Trp—Lys—Val—Cys———Cys).
         └─S—S─┘

11. A method for selectively inhibiting the release of insulin, glucagon and growth hormone which comprises administering to an animal an effective amount of a cyclic hexapeptide of claim 1.

12. A pharmaceutical composition comprising a therapeutically effective amount of the cyclic hexapeptide of claim 1 or the nontoxic acid addition salts thereof in a pharmaceutically acceptable liquid or solid carrier.

13. A compound having the formula:

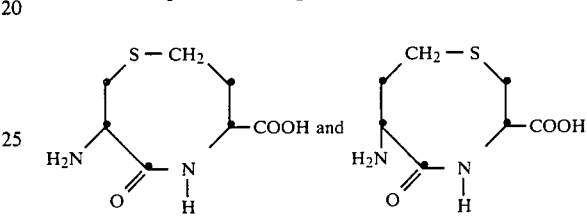

and protected derivatives thereof.

* * * * *